(12) United States Patent
Chuck et al.

(10) Patent No.: US 6,376,677 B1
(45) Date of Patent: *Apr. 23, 2002

(54) PROCESS FOR THE PREPARATION OF NICOTINIC ACID

(75) Inventors: Roderick J. Chuck, Brig-Glis; Uwe Zacher, Naters, both of (CH)

(73) Assignee: Lonza AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 09/597,244

(22) Filed: Jun. 20, 2000

Related U.S. Application Data

(62) Division of application No. 09/197,477, filed on Nov. 23, 1998, now Pat. No. 6,077,957.

(30) Foreign Application Priority Data

Nov. 25, 1997 (CH) .............................................. 2719/97

(51) Int. Cl.$^7$ ............................................ C07D 213/30
(52) U.S. Cl. ...................................... 546/319; 546/320
(58) Field of Search ................................. 546/319, 320

(56) References Cited

U.S. PATENT DOCUMENTS 3,929,811 A  12/1975  Gelbein et al. .............  546/319

FOREIGN PATENT DOCUMENTS

DE    2435134    5/1975

OTHER PUBLICATIONS

CA 130: 95133, Hayakawa et al. 1999.*

Chemical Abstracts, vol. 123, No. 24 (317458), Dec. 11, 1995 (Abstract No. 317458).

Chemical Abstracts, vol. 86, No. 19 (139772), May 9, 1977 (Abstract No. 139772).

Chemical Abstracts, vol. 86, No. 17 (121171), Apr. 25, 1977 (Abstract No. 121171).

* cited by examiner

*Primary Examiner*—Jane Fan
(74) *Attorney, Agent, or Firm*—Fisher, Christen & Sabol

(57) ABSTRACT

Nicotinic acid is produced from aqueous solutions of ammonium nicotinate by spray-drying. The nicotinic acid can be freed from residual ammonium nicotinate by a thermal post-treatment in a fluidized bed or under reduced pressure. The process is suitable in particular for the work-up of the reaction mixture produced in the oxidation of 3-methylpyridine with atmospheric oxygen, with the ammonia and, if appropriate, the water, being able to be recycled. Nicotinic acid ("vitamin PP") is an important additive to foodstuffs and feedstuffs.

12 Claims, 1 Drawing Sheet

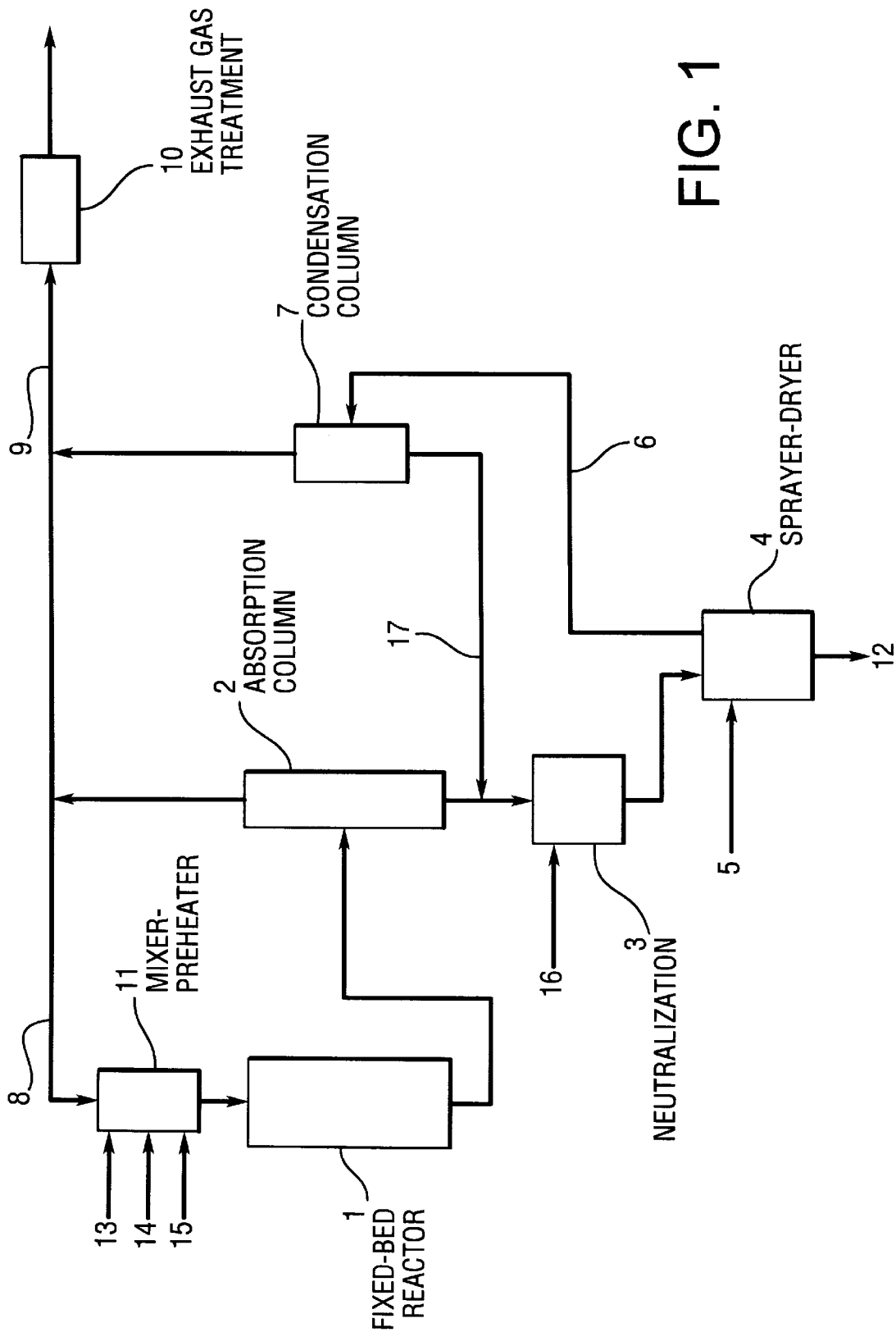

PROCESS FOR THE PREPARATION OF NICOTINIC ACID

This is a division of U.S. Ser. No. 09/197,477, filed on Nov. 23, 1998, now U.S. Patent No. 6,077,957, issued on Jun. 20, 2000, that has priority benefit of Swiss Patent Application No. 2719/97, filed on Nov. 25, 1997.

BACKGROUND OF THE INVENTION

1. Field of The Invention

The invention relates to a process for preparing nicotinic acid from solutions of ammonium nicotinate.

2. Background Art

A known process for preparing nicotinic acid is based on the oxidation of 3-methylpyridine (β-picoline) with atmospheric oxygen in the presence of water with heterogeneous catalysis. However, such process has the disadvantage that, in a side reaction, some of the 3-methylpyridine is broken down in a sequence of oxidation and hydrolysis steps to form ammonia, which, together with the main product nicotinic acid, forms ammonium nicotinate. The latter, in contrast to the free nicotinic acid, is highly water soluble and thus makes the work-up of the product mixture more difficult, and furthermore it represents a loss in yield, if it cannot be converted back to nicotinic acid. The latter is possible, for example, by adding a strong acid, but this forms the ammonium salt of this acid, which must be separated off and disposed of as waste. In addition, it must be noted here that nicotinic acid, as a pyridine derivative, can also react as a base and, with an excess of the strong acids, can form a salt.

BROAD DESCRIPTION OF THE INVENTION

The object of the invention is to provide a process which permits the transformation of ammonium nicotinate to nicotinic acid without adding auxiliaries and without producing wastes. According to the invention this object is achieved by the process according to the invention.

It has surprisingly been found that an aqueous solution of ammonium nicotinate can be converted to nicotinic acid by spray-drying. In this process, the ammonia, together with the water, escapes in the exhaust gas of the spray-dryer,

DETAILED DESCRIPTION OF THE INVENTION

The spray-drying is preferably carried out at a drying gas temperature (at the inlet) of from 160° to 250° C. A suitable drying gas is air or an inert gas, such as, nitrogen or argon. The outlet temperature is advantageously kept below 110° C. in order to prevent sublimation of the product.

Preferably, the spray-drying is carried out in a fluidized-bed spray-dryer. Fluidized-bed spray-dryers of this type are available under the name FSD™, for example, from Niro A/S in DK-2860 Søborg, Denmark.

The nicotinic acid obtained after the spray-drying still contains small amounts of ammonium nicotinate, depending on the drying temperature. It has been found that this can be further decreased by a thermal post-treatment in a fluidized bed at from 100° to 200° C., preferably from 130° to 170° C. Any nicotinic acid dust produced in this treatment can be recirculated to the spray-dryer.

As an alternative to this post-treatment in the fluidized bed, post-treatment under reduced pressure (partial vacuum or vacuum) at relatively low temperature can also be carried out. The pressure employed in this case is advantageously below 100 mbar, preferably below 50 mbar. The temperature in this case is expediently from 70° to 150° C., preferably from 80° to 120° C. Particularly good results have been achieved at from 10 to 15 mbar, from 80° to 90° C. and a treatment time of from ½ to 1 hour. At this low temperature, the losses due to sublimation are minimal and a product having excellent transparency, that is, no discoloration, is obtained.

Preferably, the process according to the invention is carried out using an ammonium nicotinate solution which was obtained by adding ammonia to the, possibly concentrated, aqueous crude solution from the catalytic oxidation of 3-methylpyridine. This can be achieved, for example, by metering gaseous or aqueous ammonia into an absorption column, to which is fed the gaseous reaction mixture from the oxidation reactor and from which the ammonium nicotinate solution is taken off as bottom product and the excess water is taken off overhead.

The ammonia needed to prepare the ammonium nicotinate solution is in this case preferably wholly or partly withdrawn from the spray-drying exhaust gas. For this purpose, for example, the dryer exhaust gas can be cooled below the dew point and the condensing ammonia water can be separated off and recirculated to the nicotinic acid absorption. Since, as mentioned above, small amounts of ammonia are produced in any case as a by-product in the oxidation of 3-methylpyridine, overall an ammonia excess is produced, so that with sufficient efficiency of the ammonia recycling, in the continuous operation, feed of external ammonia can be dispensed with completely.

Likewise, the water present in the spray-drying exhaust gas is preferably completely or partially recirculated to the oxidation reactor. Since, in the oxidation of 1 mol of 3-methylpyridine to nicotinic acid, in the ideal case, 1 mol of water is produced, a small excess of water is produced, which must be discharged from the plant in a suitable manner. Similarly, any unreacted 3-methylpyridine present is advantageously recycled to the oxidation reactor. Furthermore, it is possible to feed pure oxygen instead of air as oxidizing agent in the steady state to a continuous plant for carrying out the process according to the invention and to circulate the drying gas, so that a plant with minimum production of exhaust gas results.

An advantage of the process according to the invention is also that the nicotinic acid thus obtainable is free-flowing without additional treatment and virtually has no tendency to clumping even at high temperature and relative humidity. Furthermore, by varying the spray-drying operating parameters the particle size of the product can be set to the desired value.

BRIEF DESCRIPTION OF THE DRAWING

In the drawing:

FIG. 1 shows diagrammatically as an example a continuous plant suitable for carrying out the process according to the invention.

DETAILED DESCRIPTION OF THE DRAWING

In FIG. 1, individually, the reference numbers denote the following:

1 fixed-bed reactor together with catalyst
2 absorption column for partial condensation of the reaction mixture
3 neutralization (addition of ammonia)

4 spray-dryer
5 drying gas feed (hot air or inert gas circulation)
6 spray-dryer exhaust gas
7 column for partial condensation of water and ammonia
8 gas recycle to the reactor
9 exhaust gas for exhaust gas treatment
10 exhaust gas treatment (combustion)
11 mixer/preheater
12 product take-off (nicotinic acid)
13 3-methylpyridine feed to the reactor
14 oxygen feed (air) to the reactor
15 water (steam) feed to the reactor
16 ammonia feed to the neutralization
17 ammonia (water) recycle.

EXAMPLES

The following examples illustrate the procedure of the process according to the invention without a restriction to be understood therefrom Example 1

15 l/h of an aqueous ammonium nicotinate solution (40 percent by weight nicotinic acid and 6 percent by weight ammonia) was sprayed into a fluidized-bed spray-dryer (Niro FSD™-4. diameter 1.2 m, height 2.5 m), The drying gas (nitrogen) inlet temperature was 220° C., and the outlet temperature was 100° C. The internal fluidized-bed temperature was 70° C. This produced a free-flowing product comprising 89 percent by weight nicotinic acid and 11 percent by weight ammonium nicotinate having a residual moisture of 0.05 percent, a bulk density of 0.4 kg/l and a mean particle size of 451 μm.

Example 2

The spray-dried granules of nicotinic acid obtained in accordance with Example 1 were heated to a maximum of 170° C. with air in the course of 45 min in a fluidized bed. The granules thus treated had a nicotinic acid content of 99.3 percent and a bulk density of 0.44 kg/l. It was still free-flowing even after storage of 48 hours at 50° C. and 100 percent relative humidity.

Example 3

From the condensate of the reaction mixture of the gas-phase oxidation of 3-methylpyridine with air in the presence of water on a fixed-bed catalyst, with addition of ammonia, an approximately 30 percent strength solution of ammonium nicotinate was produced. This solution was sprayed in a laboratory spray-dryer (Büchi AG, Switzerland). At a drying gas inlet temperature of 250° C. and an outlet temperature of 162° C., nicotinic acid having a content of from 99 to 100 percent was obtained at a nitrogen flow rate of 800 ml/min.

At an inlet temperature of 200° C. and an outlet temperature of 130° C., nicotinic acid having a content of 96.9 percent was obtained at a nitrogen flow rate of 600 ml/min.

What is claimed is:

1. In a process for preparing nicotinic acid comprising spray-drying an aqueous solution of ammonium nicotinate with a drying gas to remove ammonia produced, the improvement of subjecting the nicotinic acid produced above with a thermal post-treatment at a temperature of 70 to 150° C. and a pressure below 100 mbar.

2. The process according to claim 1 wherein the thermal post-treatment is conducted at a temperature of 80 to 120° C.

3. The process according to claim 1 wherein the thermal post-treatment is conducted at a pressure of 10 to 15 mbar, at a temperature of 80 to 90° C., and with a treatment time of one-half to one hour.

4. The process according to claim 1, wherein the thermal post-treatment is conducted at below 50 mbar and at a temperature of 80 to 120° C.

5. The process according to claim 1, wherein the spray-drying is carried out in a fluidized bed spray dryer.

6. The process according to claim 1, wherein the aqueous solution of ammonium nicotinate used is produced by adding ammonia to the aqueous crude solution obtained by the catalytic oxidation of 3-methylpyridine.

7. The process according to claim 6, wherein the water present in the spray-drying exhaust gas is wholly or partly recycled to the oxidation reactor.

8. The process according to claim 6, wherein the ammonia for preparing the ammonium nicotinate solution is wholly or partially withdrawn from the spray-drying exhaust gas.

9. The process according to claim 8, wherein the water present in the spray-drying exhaust gas is wholly or partly recycled to the oxidation reactor.

10. The process according to claim 1, wherein the spray-drying is conducted at a temperature of 160 to 250° C.

11. The process according to claim 1, wherein the drying gas is hot air or hot inert gas.

12. The process according to claim 2, wherein the hot inert gas is nitrogen.

* * * * *

(12) EX PARTE REEXAMINATION CERTIFICATE (9496th)

United States Patent
Chuck et al.

(10) Number: US 6,376,677 C1
(45) Certificate Issued: *Jan. 28, 2013

(54) PROCESS FOR THE PREPARATION OF NICOTINIC ACID

(75) Inventors: Roderick J. Chuck, Brig-Glis (CH); Uwe Zacher, Naters (CH)

(73) Assignee: Lonza AG, Gampel/Valais (CH)

Reexamination Request:
No. 90/011,246, Sep. 21, 2010

Reexamination Certificate for:
Patent No.: 6,376,677
Issued: Apr. 23, 2002
Appl. No.: 09/597,244
Filed: Jun. 20, 2000

(*) Notice: This patent is subject to a terminal disclaimer.

Related U.S. Application Data

(62) Division of application No. 09/197,477, filed on Nov. 23, 1998, now Pat. No. 6,077,957.

(30) Foreign Application Priority Data

Nov. 25, 1997 (CH) .......................................... 2719/97

(51) Int. Cl.
*C07D 213/00* (2006.01)
*C07D 213/79* (2006.01)
*C07D 213/803* (2006.01)

(52) U.S. Cl. ....................................... 546/319; 546/320

(58) Field of Classification Search .................... None
See application file for complete search history.

(56) References Cited

To view the complete listing of prior art documents cited during the proceeding for Reexamination Control Number 90/011,246, please refer to the USPTO's public Patent Application Information Retrieval (PAIR) system under the Display References tab.

*Primary Examiner* — Dwayne Jones

(57) ABSTRACT

Nicotinic acid is produced from aqueous solutions of ammonium nicotinate by spray-drying. The nicotinic acid can be freed from residual ammonium nicotinate by a thermal post-treatment in a fluidized bed or under reduced pressure. The process is suitable in particular for the work-up of the reaction mixture produced in the oxidation of 3-methylpyridine with atmospheric oxygen, with the ammonia and, if appropriate, the water, being able to be recycled. Nicotinic acid ("vitamin PP") is an important additive to foodstuffs and feedstuffs.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-12 is confirmed.

\* \* \* \* \*